United States Patent
Gao et al.

(10) Patent No.: US 10,272,217 B2
(45) Date of Patent: Apr. 30, 2019

(54) DEVICE FOR GRIPPING AND DIRECTING BOUGIES FOR INTUBATION

(71) Applicants: Boyi Gao, Fox Point, WI (US); Nancy Gao, Fox Point, WI (US); Hua Gao, Fox Point, WI (US)

(72) Inventors: Boyi Gao, Fox Point, WI (US); Nancy Gao, Fox Point, WI (US); Hua Gao, Fox Point, WI (US)

( * ) Notice: Subject to any disclaimer, the term of this patent is extended or adjusted under 35 U.S.C. 154(b) by 716 days.

(21) Appl. No.: 14/962,141

(22) Filed: Dec. 8, 2015

(65) Prior Publication Data

US 2017/0157349 A1    Jun. 8, 2017

(51) Int. Cl.
| | | |
|---|---|---|
| A61M 16/04 | (2006.01) | |
| A61B 1/00 | (2006.01) | |
| A61B 1/018 | (2006.01) | |
| A61B 1/267 | (2006.01) | |

(52) U.S. Cl.
CPC .... *A61M 16/0488* (2013.01); *A61M 16/0463* (2013.01); *A61B 1/00147* (2013.01); *A61B 1/018* (2013.01); *A61B 1/267* (2013.01); *A61M 2202/0208* (2013.01); *A61M 2205/586* (2013.01)

(58) Field of Classification Search
CPC ............. A61M 16/04; A61M 16/0418; A61M 16/0429; A61M 16/0463; A61M 16/0465; A61M 16/0488; A61M 16/0493; A61M 16/0497; A61M 2205/586; A61M 25/01; A61M 25/0102; A61M 25/018; A61M 2025/0177; A61M 2025/0188; A61M 31/00; A61B 1/00094; A61B 1/267; A61B 1/2673; A61B 1/2676

See application file for complete search history.

(56) References Cited

U.S. PATENT DOCUMENTS

| | | | |
|---|---|---|---|
| 3,802,440 A * | 4/1974 | Salem | A61M 16/0488 |
| | | | 128/200.26 |
| 4,211,234 A | 7/1980 | Fisher | |
| 4,502,482 A | 3/1985 | DeLuccia et al. | |
| 4,699,138 A | 10/1987 | Behrstock | |
| 4,865,586 A | 9/1989 | Hedberg | |
| 4,892,095 A | 1/1990 | Nakhgevany | |
| 5,016,614 A | 5/1991 | MacAllister | |
| 5,058,577 A | 10/1991 | Six | |
| 5,257,620 A | 11/1993 | Schermerhorn | |

(Continued)

FOREIGN PATENT DOCUMENTS

| | | | | |
|---|---|---|---|---|
| GB | 2542640 A * | 3/2017 | ............. | A61B 1/267 |
| WO | WO 2011012677 A1 * | 2/2011 | ......... | A61B 1/00073 |

OTHER PUBLICATIONS

Machine translation of WO 2011012677 A1.*

*Primary Examiner* — Jan Christopher L Merene
*Assistant Examiner* — Joseph D. Boecker
(74) *Attorney, Agent, or Firm* — Ryan Kromholz & Manion, S.C.

(57) ABSTRACT

An apparatus for endotracheal intubation. The apparatus allows medical personnel to grip and stabilize a bougie inside the apparatus and maintain a curve position during intubation processes. The apparatus can be used for a solid bougie and/or a hollow bougie. The apparatus may further have a connector for connecting the apparatus to an external suction device or oxygen delivery device.

19 Claims, 9 Drawing Sheets

(56) References Cited

U.S. PATENT DOCUMENTS

| | | | |
|---|---|---|---|
| 5,287,848 A * | 2/1994 | Cubb | A61M 16/0488 |
| | | | 128/200.26 |
| 5,520,175 A | 5/1996 | Fry | |
| 5,595,172 A | 1/1997 | Reese | |
| RE35,595 E | 8/1997 | Six | |
| 5,842,973 A * | 12/1998 | Bullard | A61M 16/0488 |
| | | | 600/194 |
| 6,146,402 A | 11/2000 | Munoz | |
| 7,243,653 B2 | 7/2007 | Nelson | |
| 8,161,967 B2 | 4/2012 | Harms et al. | |
| 10,080,854 B1 * | 9/2018 | Pifer | A61M 16/0463 |
| 2007/0017527 A1 * | 1/2007 | Totz | A61M 16/04 |
| | | | 128/207.15 |
| 2008/0276932 A1 * | 11/2008 | Bassoul | A61M 16/04 |
| | | | 128/200.26 |
| 2010/0121152 A1 * | 5/2010 | Boedeker | A61B 1/00094 |
| | | | 600/187 |
| 2010/0249513 A1 * | 9/2010 | Tydlaska | A61B 1/00052 |
| | | | 600/186 |
| 2012/0065471 A1 * | 3/2012 | McGrath | A61B 1/267 |
| | | | 600/114 |
| 2014/0238390 A1 * | 8/2014 | Wei | A61M 16/0488 |
| | | | 128/200.26 |
| 2016/0038014 A1 * | 2/2016 | Molnar | A61M 16/0003 |
| | | | 600/109 |
| 2017/0224200 A1 * | 8/2017 | Uesugi | A61B 1/00147 |
| 2017/0246410 A1 * | 8/2017 | Levitan | A61B 1/267 |
| 2017/0325667 A1 * | 11/2017 | Alonso Babarro | |
| | | | A61B 1/00147 |
| 2018/0318534 A1 * | 11/2018 | Desatnik | A61M 16/0418 |

\* cited by examiner

DEVICE FOR GRIPPING AND DIRECTING BOUGIES FOR INTUBATION

BACKGROUND OF THE INVENTION

The present invention relates to a bougie device and method of use thereof, and more particularly relates to a device for gripping and directing a bougie device which is suitable for guiding insertion of an endotracheal tube into an airway of a person.

A bougie may have numerous uses in medicine, but are commonly used to widen a passageway or guide another instrument into a passageway. An intubation aide commonly known as the "gum elastic bougie" is a thin, solid or hollow, cylinder of rubber, plastic or another material that a physician inserts into a body passageway. Within the art of tracheal intubation, bougies are frequently used as a guide for the correct placement of an endotracheal tube. Bougies are also used to provide suction or oxygen delivery within a body passageway.

Bougies generally require a necessary level of flexibility so that they can navigate a body passageway, with the required flexibility resulting in bougies that are hard to grip. Devices have been designed to assist in intubation of the bougie, i.e. guiding the bougie, but such devices still have limitations in allowing for adequate gripping of the bougie so that it can be properly navigated during a procedure.

In many medical situations endotracheal intubation is a critical procedure performed to secure a patient's airway. To facilitate insertion of an endotracheal tube, a physician, paramedic or other medical personnel will use a laryngoscope blade which is inserted down a patient's throat. The laryngoscope blade is primarily used to move the tongue and the epiglottis from the providers view in order to provide a clear passage to the vocal cords. Placement of the endotracheal tube correctly in the patient's trachea must be done quickly to avoid hypoxic brain injury to the patient. The task of endotracheal intubation becomes more challenging in emergent situations, patients with difficult airways and those that are at high risk for aspiration.

Commonly in the operating room prior to induction of general anesthesia patients are given 100% oxygen to breath in effort to replace nitrogen in the lungs with oxygen. This process is known as preoxygenation and serves to fill the lungs with oxygen like a reservoir. When patients undergo general anesthesia they become apneic and must rely on the oxygen reservoir within the lungs to provide oxygen for the bodies basic metabolic needs. Sufficient preoxygenation adequately fills the lungs with oxygen to provide more time for the medical personnel to instrument the airway and attempt endotracheal intubation.

Evaluation of a patient's airway allows physicians to gauge the difficulty that may be encountered when attempting endotracheal intubation. Certain clinical features of patient such a large neck circumference, obesity, history of sleep apnea, small mouth opening, and overbite among, others are predictors of a difficult endotracheal intubation. Once a patient has been deemed to have a difficult airway, the physician may obtain equipment such as a video laryngoscope or intubation aide like the bougie. A physician may have a poor view of a patient with a difficult airway of the vocal cords under direct laryngoscopy, which would make endotracheal intubation difficult. The bougie is vital tool in the difficult airway as it has a bended tip that facilitates its passage into the patient's trachea.

Commonly found within hospitals is suction tubing with a handle attached, also known as a yankauer, which are used to aspirate fluid within the patient's airway. Under direct laryngoscopy, the yankauer provides direct vision of the patient's vocal cords. In an effort to overcome these problems, medical personnel often insert the yankauer to remove blood, oral secretions, or gastric content prior to proper placement of the endotracheal tube. After aspiration of fluid within the pharynx the suction device must be removed and an endotracheal tube must be inserted within the trachea. This two step procedure of clearing secretions, gastric contents, or blood with the suction tube removing it and then grabbing an endotracheal tube results in lost time. However, these prior art processes use valuable time, along with the patient's oxygen reservoir, switching between devices. Moreover, even when suction tube is inserted into the mouth it is possible fluids to reaccumulate in between the time suction tube is removed and endotracheal tube insertion.

If an intubation attempt fails, then the patient must be ventilated with bag and mask device which can force air down the trachea as well as down the esophagus. When the stomach is extended with air, patient becomes more likely to vomit and aspirate. A distended abdomen also decreases a patient's lung compliance and makes it more difficult to ventilate. Moreover, repeated intubation involves instrumenting the airway with laryngoscope blade which causes trauma to the patient which can result in bleeding and edema. It is vital that endotracheal intubation be accomplished quickly, accurately, atraumatically and on consistently on the first attempt. Repeated attempts with intubation often make endotracheal intubation even more challenging. A distended abdomen from bag-mask ventilation, bleeding, or edema can obstruct the physician's view of the vocal cords and places the patient at risk for aspiration. This is a common problem with the current intubation procedure with a difficult airway has been taking time to exchange between using the bougie, yankauer, and the endotracheal tube. This lost time puts the patient at risk for aspiration pneumonia, aspiration pneumonitis, or hypoxic brain injury.

U.S. Pat. No. 5,257,620 describes an airway device that has a suction stylet that telescopically disposed therein and attached to the endotracheal tube. The suction stylet is connected to a suction source which allows suction forces to withdraw fluids continuously. During the intubation process, if continuous suction forces at the distal suction stylet are present it can cause trauma to the vocal cords. Furthermore, a suction device that lacks complete control by the provider may be problematic as continuous suction in the oropharynx will also remove oxygen from the patient. Continuous suction of oxygen from the patient oropharynx will hasten the development of hypoxia. This takes away valuable time the provider has when attempting to intubate the patient and must revert to bag-mask ventilation. As hypoxia develops patients are at risk for developing anoxic brain injury and even cardiac arrest.

U.S. Pat. No. 5,595,172 describes a device that includes a suction stylet that is inserted into an endotracheal tube and allows the provider to control suction. The stylet has a main body with a central passageway along the main body and a vent arm that extends off the main body. The vent arm has a vent port that allows the provider to utilize suction with occlusion of the vent port. This device may offer a suction stylet that can be only be used to clear secretions but does not function as an intubation aide.

SUMMARY OF THE INVENTION

The present invention provides a gripping device for a solid or hollow bougie or bougies during an intubation procedure. The hollowed bougie can be connected to external tubing, e.g. suction tubing or oxygen tubing.

The present invention may further comprise a suction bougie that can be used to aspirate fluids as well as an intubation guide for insertion of an endotracheal tube into the airway of a patient. Commonly, when a medical personnel performs a direct laryngoscopy of a patient's airway to assess for adequate visualization of the vocal cords, the presence of oral sections, blood, masses, or gastric contents. The airway device mentioned above is primarily used for patients with a difficult airway, or who are at risk for aspiration of gastric contents. Management of these patients often necessitates that an intubation guide commonly known in the field as gum elastic "bougie" and an oral suction device. The bougie may be used if there is poor visualization of the vocal cords and a suction apparatus is needed to clear oral secretions or gastric contents to provide an unobstructed view of the vocal cords. The use of either the bougie or suction requires the medical personnel to switch between handling either device. The proposed invention allows the medical personnel to use the bougie and suction simultaneously without having to spend time to exchange devices. This ultimately removes inherent delays in securing the airway.

The invention as mentioned functions as an apparatus that attaches to a bougie to facilitate endotracheal intubation. The apparatus may be attached to a pre-existing bougie intubation aid as well a suction bougie. The suction bougie is designed as a hollow tube to be used as a suction bougie. The suction bougie may comprise of an elongated body that is hollow at both the proximal and distal ends. The distal of the tube would have several open ports to allow for passage of oral secretions, blood, or gastric contents. The proximal end would be connected to a curved bougie holder. The body of the bougie device may be formed from Teflon, polytetrafluoroethylene, or plastic polymer which would result in a self lubricated device. This would reduce the need for the bougie device to be lubricated for insertion into the airway of a patient.

The present invention is designed with a curved handle that has a curved side opening, e.g. a channel, to receive either a solid or hollow bougie. The curved handle preferably will generally be rigid and preferably manufactured from a hard plastic material.

The proximal end of the handle will encompass a hollow tube with one end to be attached to the proximal end of the suction bougie or an oxygen delivery bougie. The handle is designed with a curved and enclave where the bougie is meant to reside within with an outside force, i.e. the gripping force of the user's fingers, which allows the bougie to be moved to a curved patter, and also stabilizes the bougies by increasing the gripping area during intubation. After the bougie is attached to the proximal end of the handle, the bougie will then be bent around itself with its distal portion nestled within the curved handle. The other end of the hollow tube of proximal handle will be connected to suction tubing or oxygen tubing commonly found within the hospital. The hollow tube will have a vent port that when occluded by the medical personnel's finger will allow suction force from the distal tip of the suction bougie. When the vent port is not occluded there will be no suction force at the tip of the suction bougie. The importance of having a vent port allows the medical personnel to have complete control over when to utilize the suction function. Moreover, a suction device that lacks complete control by the provider because continuous suction of oxygen from the patient oropharynx may cause hypoxia. The invention can be used as an oxygen delivery device, as well.

The present invention also allows for telescopically advancement of an endotracheal tube over a bougie prior to advancement of a bougie into a patient's trachea. The endotracheal tube can be immediately advances over the bougie into the trachea.

The apparatus may be used with the pre-existing bougie to provide a more ergonomic way to use the bougie. The bougie is commonly must be manipulated by the medical personnel to incorporate a curve for endotracheal insertion. The curve of the bougie is meant to follow the natural curvature of the patient's oropharynx. However a common problem that is encounter with the bougie use has been its difficulty navigating a patient's oropharynx. The physical properties of the bougie make it flimsy and bendable which can make it difficult for the medical personnel to control. The apparatus will be designed with a curved and enclave where the bougie is nested within. Once the bougie is nested within the apparatus there will be a latch that will secure the bougie to the apparatus.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

As will be seen, the present invention overcomes many problems associated with prior art with intubation of a difficult airway, high risk of aspiration, or emergent endotracheal intubation. Upon induction of general anesthesia, unconscious patients, certain medical conditions render patients at risk for aspiration of gastric contents. Conditions like morbid obesity, diabetic gastroparesis, pregnancy, hiatal hernia, full stomach increases the risk aspiration upon induction of general anesthesia. The invention allows the operator to clear oral secretions, gastric contents, blood from the operator's field of view to safely intubate the patient.

Figure 1:
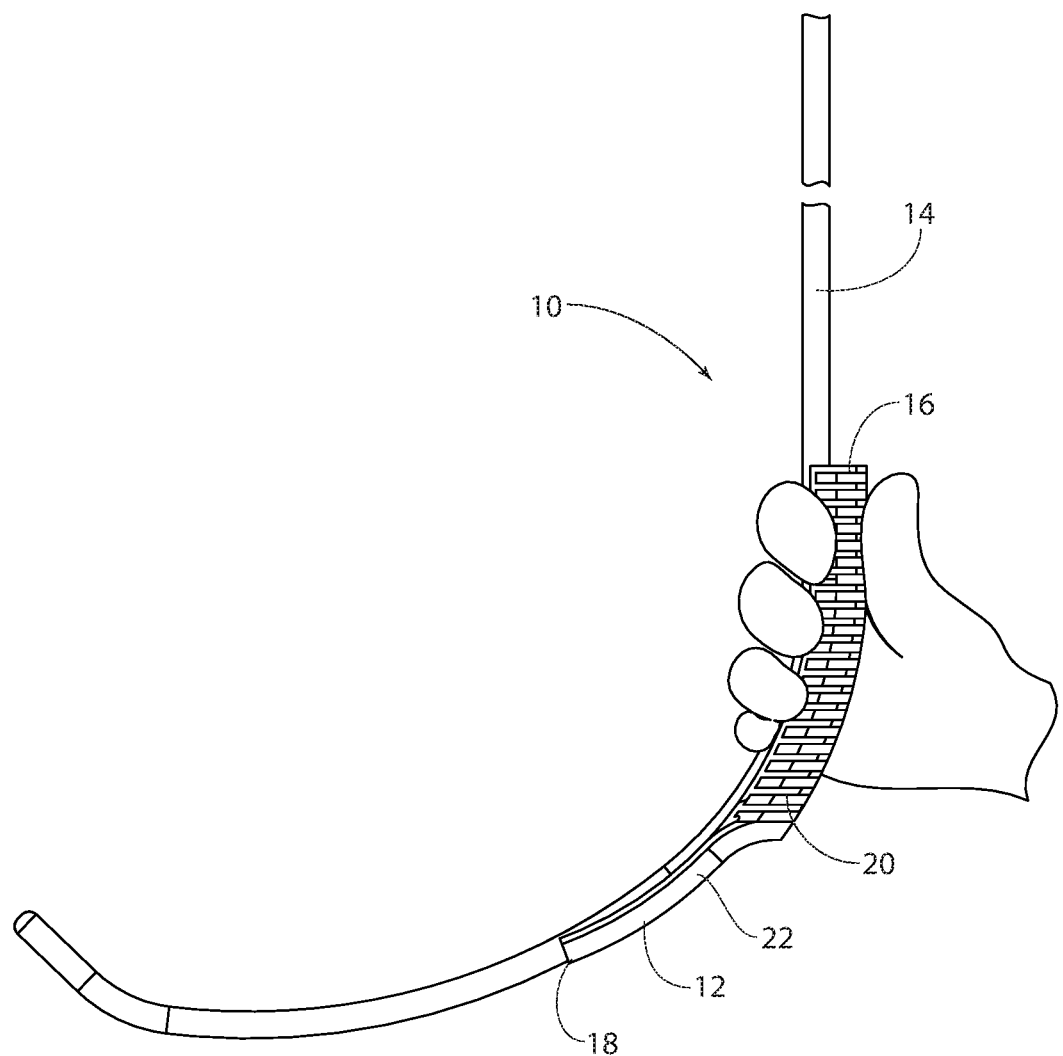
FIG. 1 is a side planar view of a gripping device according to the present invention, with a bougie attached the device.

FIG. 1 depicts an intubation control system 10 according to the present invention. The system 10 generally comprises a griping device 12 which is designed to encircle the length of a bougie 14, which is used for intubation. The gripping device 12 has a top end 16 and a bottom end 18, with a gripping surface 20 located on the outside of the gripping device 12. An extension support area 22 extends from the gripping surface 20, with the extension support area 22 also forming part of the gripping surface 20. The gripping device 12 preferably has a curvilinear shape that will be shaped to assist in inserting the bougie 14 into a passageway.

Figure 2:
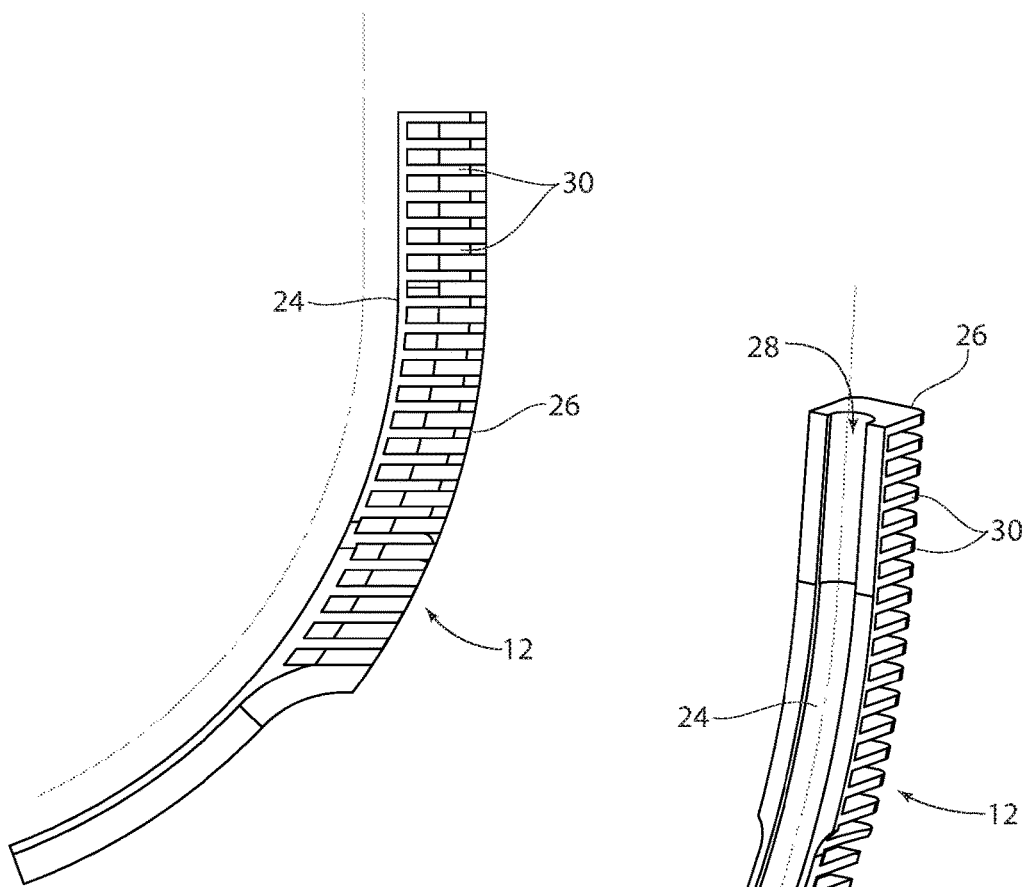
FIG. 2 is a side planar device shown in FIG. 1.
Figure 3:
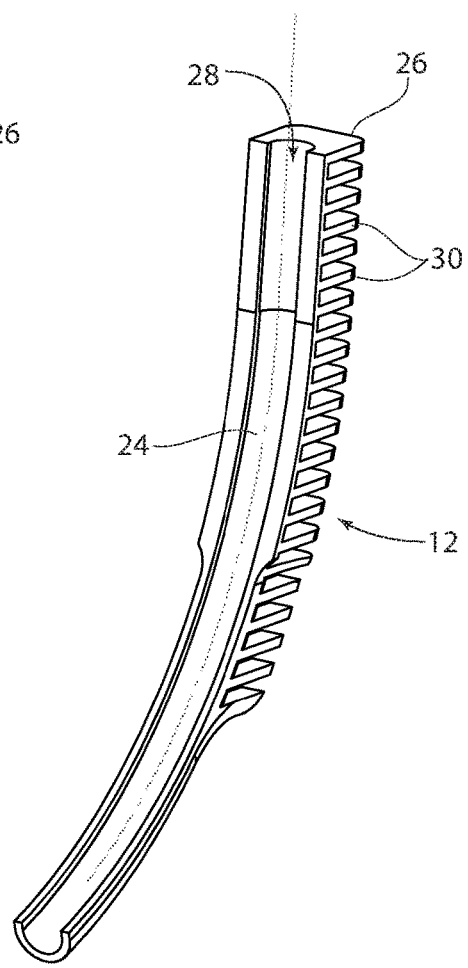
FIG. 3 is a front perspective view of the device of FIG. 1.

FIGS. 2 and 3 provide further views of the gripping device 12. The gripping device 12 further comprises an inner surface 24 and an exterior surface 26. The inner surface 24 forms an opening to receive the bougie 14. As previously noted, the inner surface 24 preferably comprises a curvilinear or longitudinally curved groove 28 shape, which can extend the length of the body. The inner surface may also comprise a semicircle shape, which will allow the bougie 14 to be nestled within the gripping device 12 and to be held in place within the gripping device 12 during an intubation process. The gripping device 12 is designed so that the bougie 14 can be forced into place by hand and, the bougie 14 will retain a curved shape with the curved groove 28 during a procedure.

Referring further to FIGS. 2 and 3, the exterior surface 20 comprises a plurality of ridges 30, which assist the user in gripping and properly holding and positioning the device 12. The ridges 30 may comprise a semi-rigid material that would conform to a user's hand, but it is understood that the exterior surface 28 may comprise any surface or arrangement, e.g. a surface contoured for fingers or a rough or textured surface, that will assist in holding the device 12.

Figure 4:
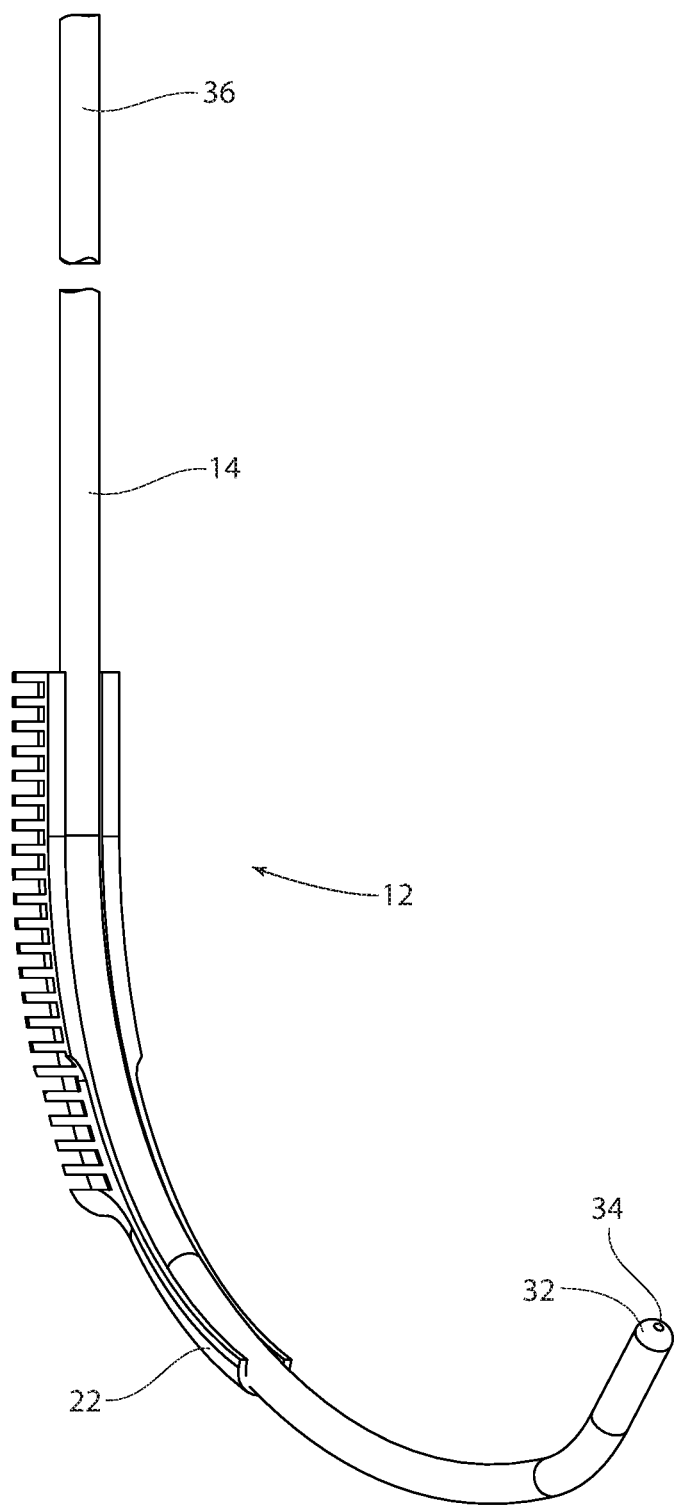
FIG. 4 is a front perspective view of the device shown in FIG. 1 with a bougie attached to the device.

Referring to FIG. 4, the device 12 is shown with the bougie 14 nestled within the groove 28. The proximal end 32 extends outward past the extension support area 22, which will allow for the proximal end 32 to be eventually intubated. As shown, the proximal end 32 has an opening 34, which allows fluid flow, e.g. air or oxygen flow, through the bougie 14 to distal end 36 of the bougie 14. The control of fluid flow by using the device 12 is discussed further, below.

Figures 5, 6:
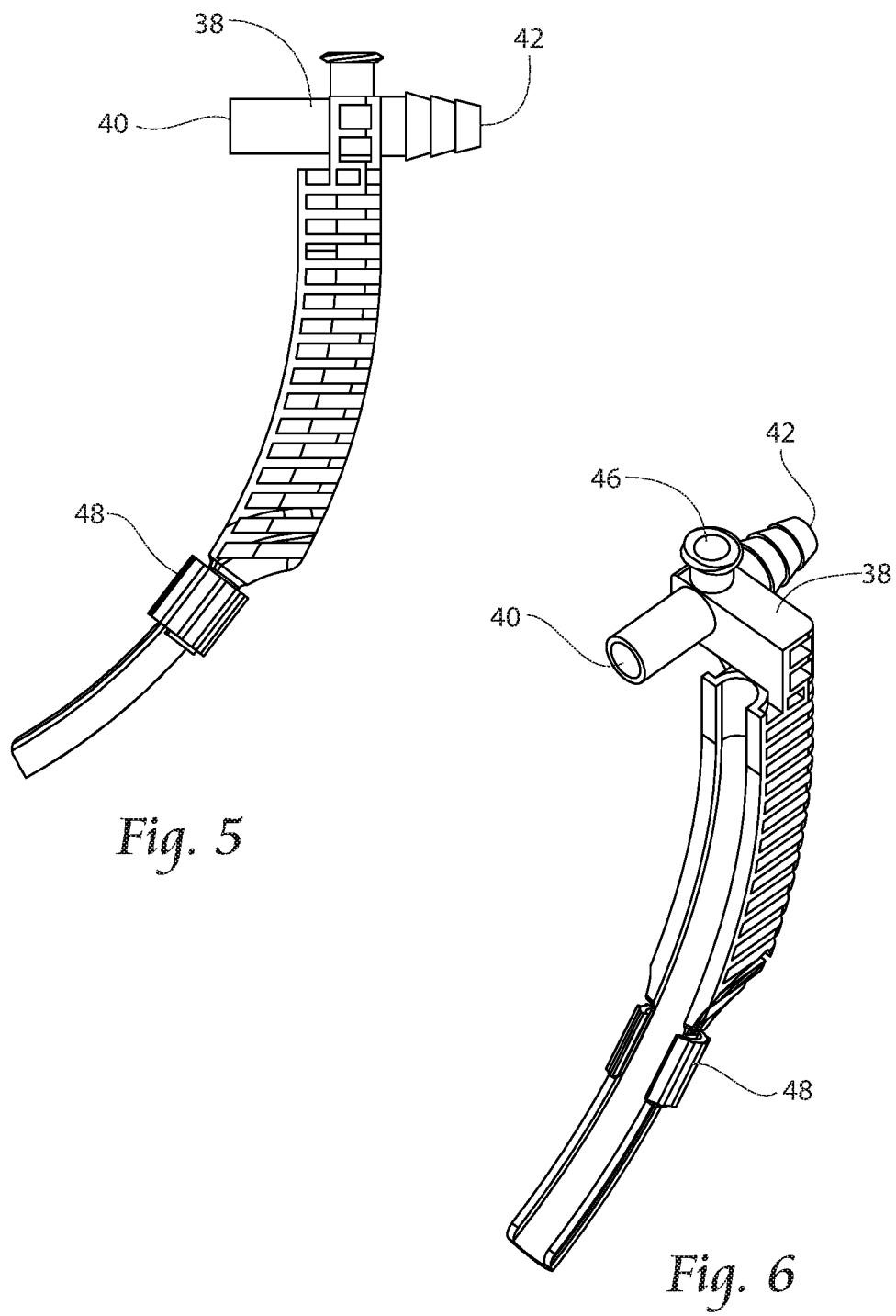
FIG. 5 is a side planar view of the gripping device of FIG. 1, with a hollow connector attached to the device.
FIG. 6 is a front perspective view of the device shown in FIG. 5, demonstrating a suction control opening.

Referring to FIGS. 5 and 6, the device 12 is shown comprising a connector 38, which assists in fluid flow through a bougie 14 when using the device 12. The connector 38 has a first end 40 and a second end 42, with a hollow passageway passing from the first end 40 to the second end 42, which allows the connector 38 to receive a bougie 14 (not shown) for fluid passage. For example, the connector 38 assists in passing oxygen through a bougie 14, or for using the bougie 14 for suction purposes. The connector 38 may also comprise a suction control opening 46, which intersects the hollow passageway in the connector 38 and allows for the user to manually control suction when the device 12 is in use.

FIGS. 5 and 6 also show another feature of the gripping device 12 that will assist in retaining a bougie within the gripping device 12. A locking ring 48 is shown on the extension support area 22. The locking ring 48, e.g. a C-ring, can be rotated so that is will hold and retain a bougie 14 in place (see FIG. 10) during an incubation process.

Figures 7, 8:
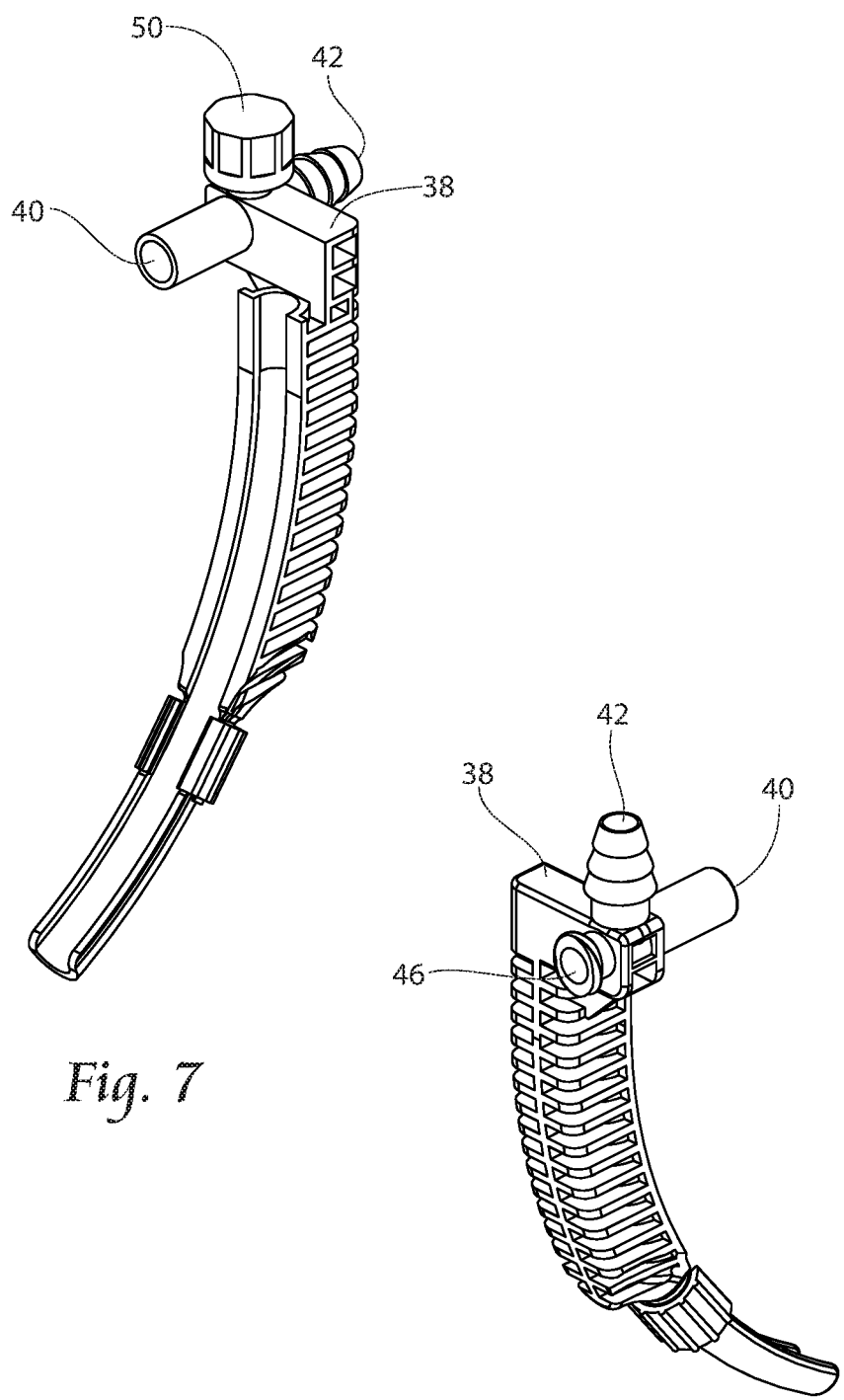
FIG. 7 is a front perspective view of the device shown in FIG. 6, with a cap located on the suction control opening.
FIG. 8 is a rear perspective view of the device of FIG. 1, with another arrangement of a hollow connector attached to the device.

FIG. 7 shows a further feature of the device 12, comprising a cap 50 located on the suction control opening 46. Such an arrangement allows for continuous suction and/or air flow, e.g. oxygen, through the bougie 14. If manual control is required, the cap 50 can be removed.

FIG. 8 demonstrates a further arrangement of the device 12 shown in FIGS. 5 and 6. The device 12 has the connector 38 located on the device 12 as previously shown and described. However, the first end 40 is perpendicular to the second end 42, and the suction control opening 46 is parallel to the first end 40. Such an arrangement may be preferable in certain instances and for certain uses. However, it is understood that the arrangements shown in FIGS. 5 and 8 operate in the same manner and can provide air or oxygen flow and/or suction as discussed, above.

Figure 9:
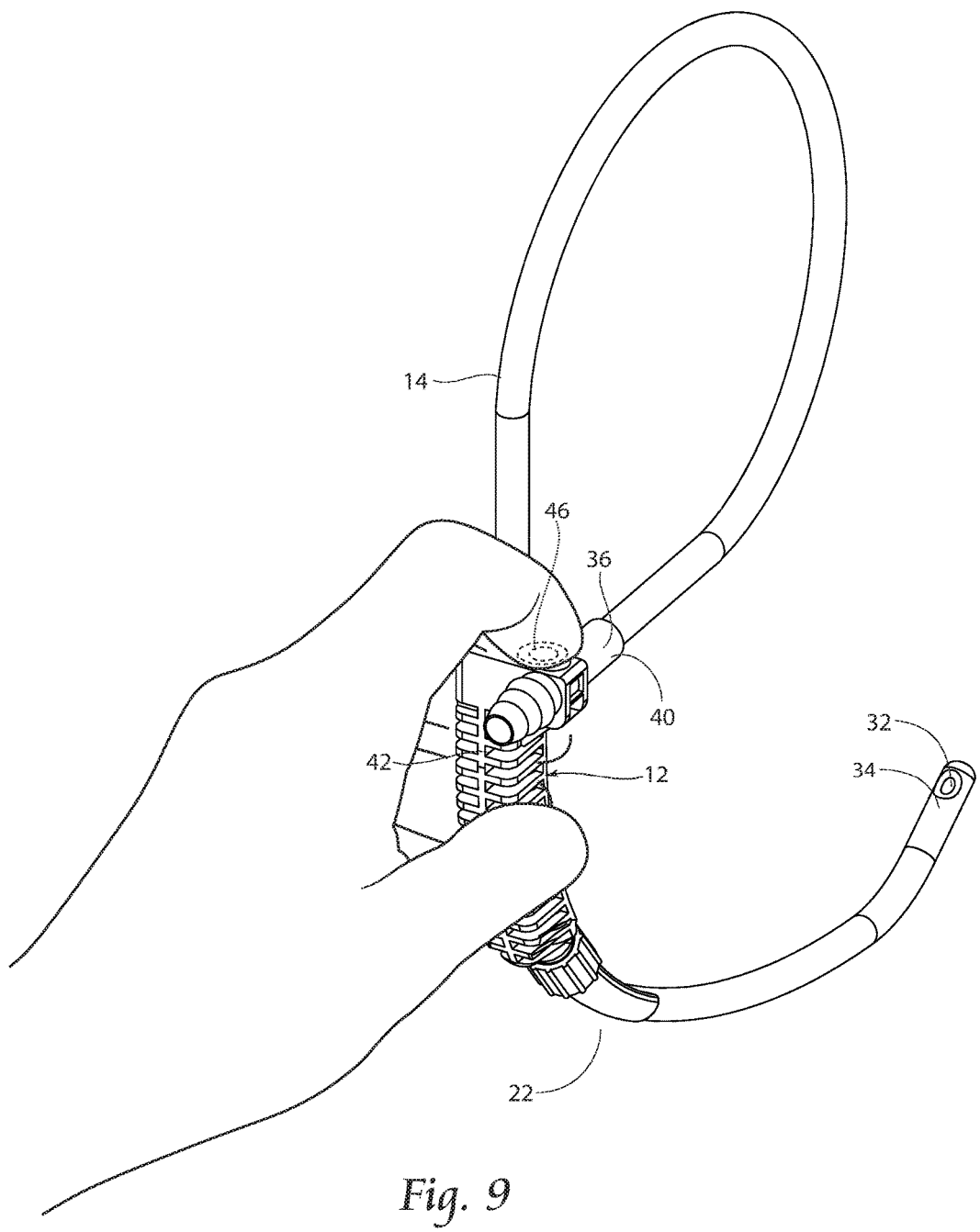
FIG. 9 is a rear perspective view of the device shown in FIG. 6, with a bougie connected to the device.

FIG. 9 demonstrates the device 12 being used as a suction tool during an intubation process. As previously discussed, a bougie 14 is positioned within the device 12. The proximal end 32 of the bougie 14 is shown extending past the extension support area 22, with the opening 34 being arranged for eventual intubation. The distal end 36 of the bougie is then positioned and inserted into the first end 40 of the connector 38. The second end 42 will be connected to an external fluid or air source (not shown), which allows the user to control suction control with the suction control opening 46. The used controls suction by placing a finger on, by either right hand or left hand, or removing a finger from, the control opening 46.

Figure 10:
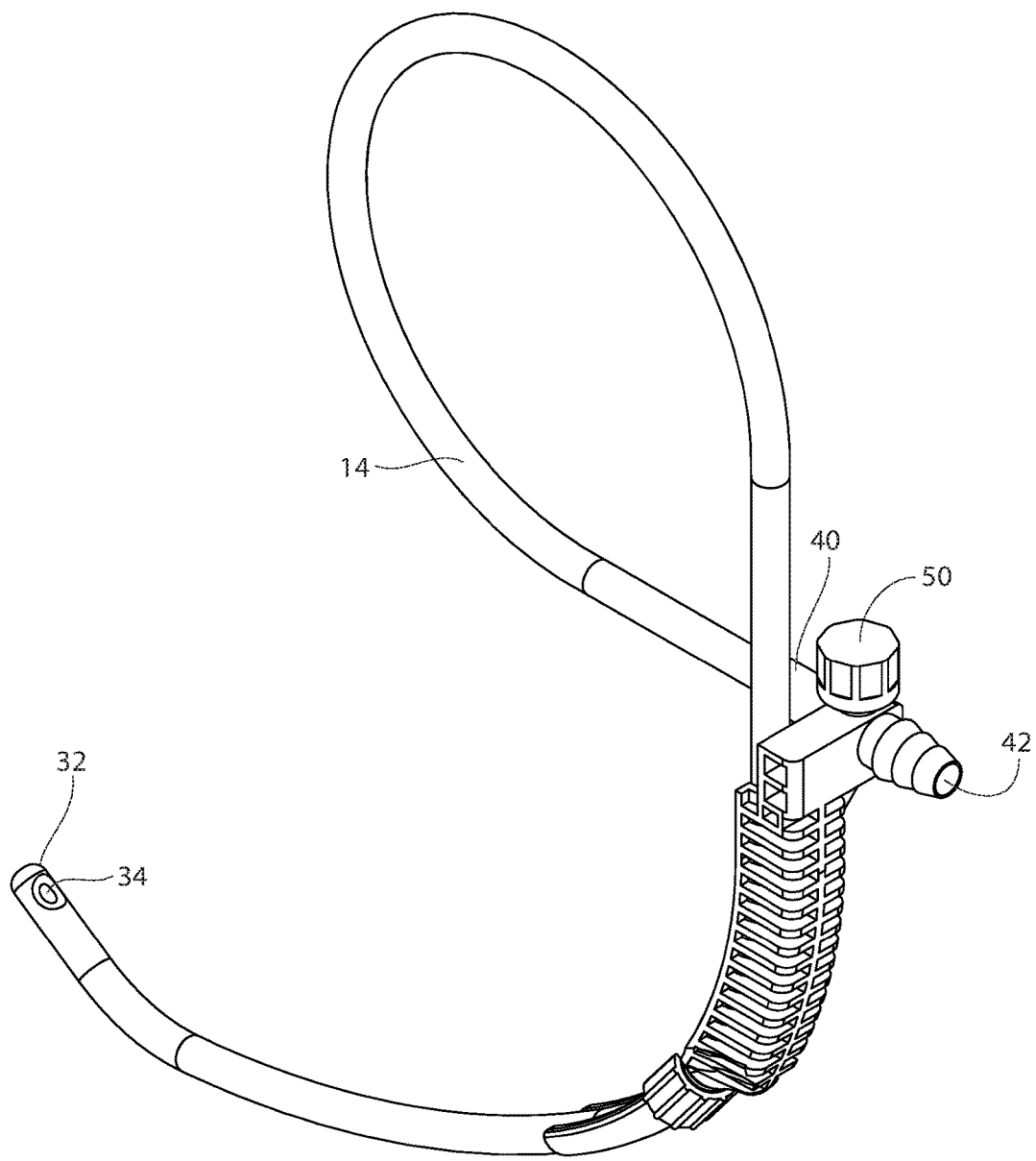
FIG. 10 is a front perspective view of the device shown in FIG. 9, with a cap located on the suction control opening.

FIG. 10 demonstrates the device 12 being used for oxygen delivery. The arrangement is similar to that shown in FIG. 9, with the exception that the cap 50 is located on the suction control opening 46. The locking ring 48 is also shown holding the bougie 14 in place. FIG. 10 also demonstrates that the bougie 14 can form a one-loop coil, which further allows for the device 12 to provide an improved gripping arrangement for intubation procedures.

Figure 11:
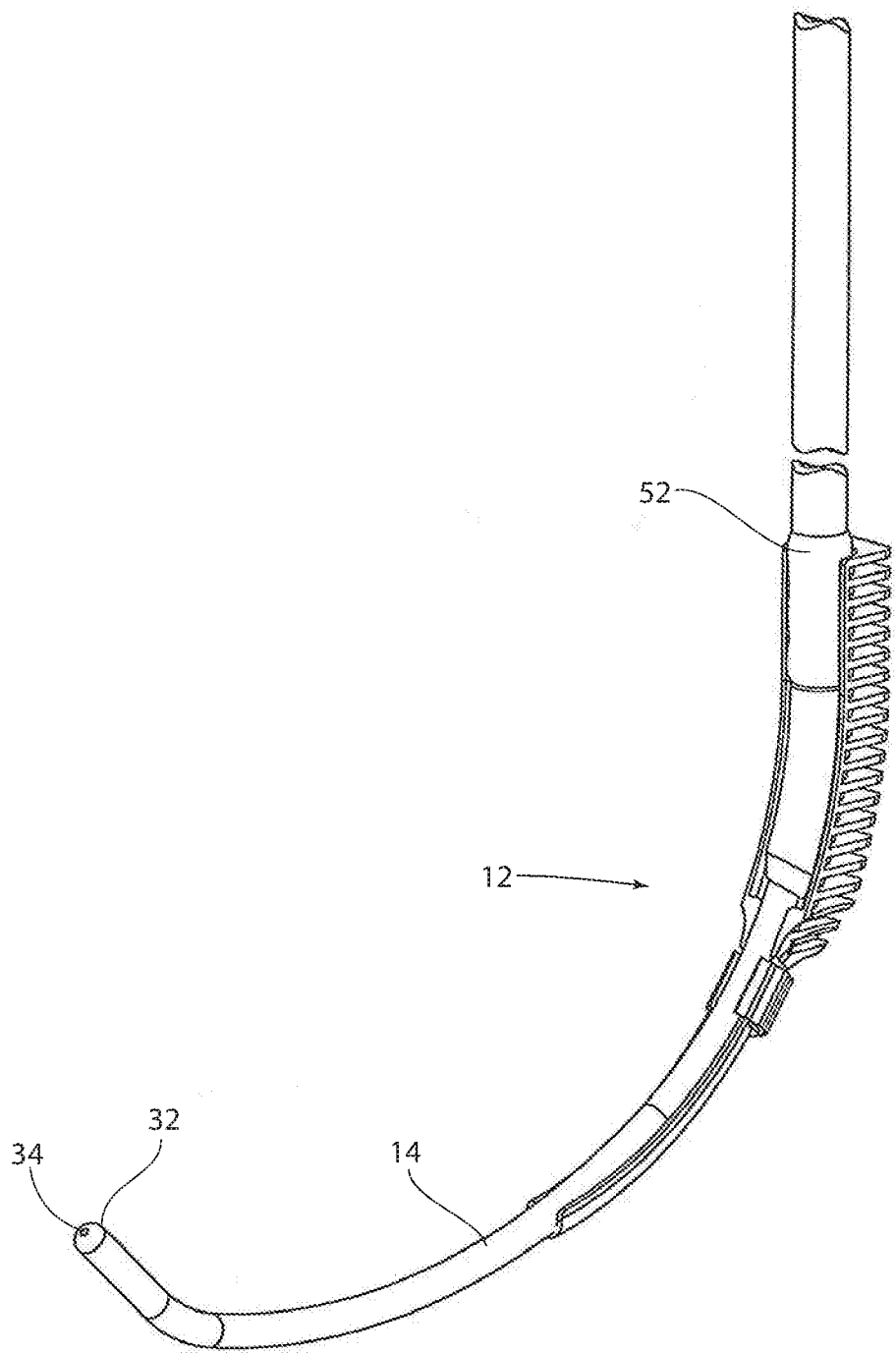
FIG. 11 is front perspective view of the device of FIG. 1 including a bougie, with means for locking the bougie within the device demonstrated.

FIG. 11 further demonstrates the adaptability of the gripping device 12. In FIG. 11, the device is shown holding both the bougie 14 and an intubation tubing 52. The device 12 can adapt so that both the tubing 52 and the bougie 14 can be nestled in the groove 28, with the locking ring 48 being used, if necessary.

Figure 12:
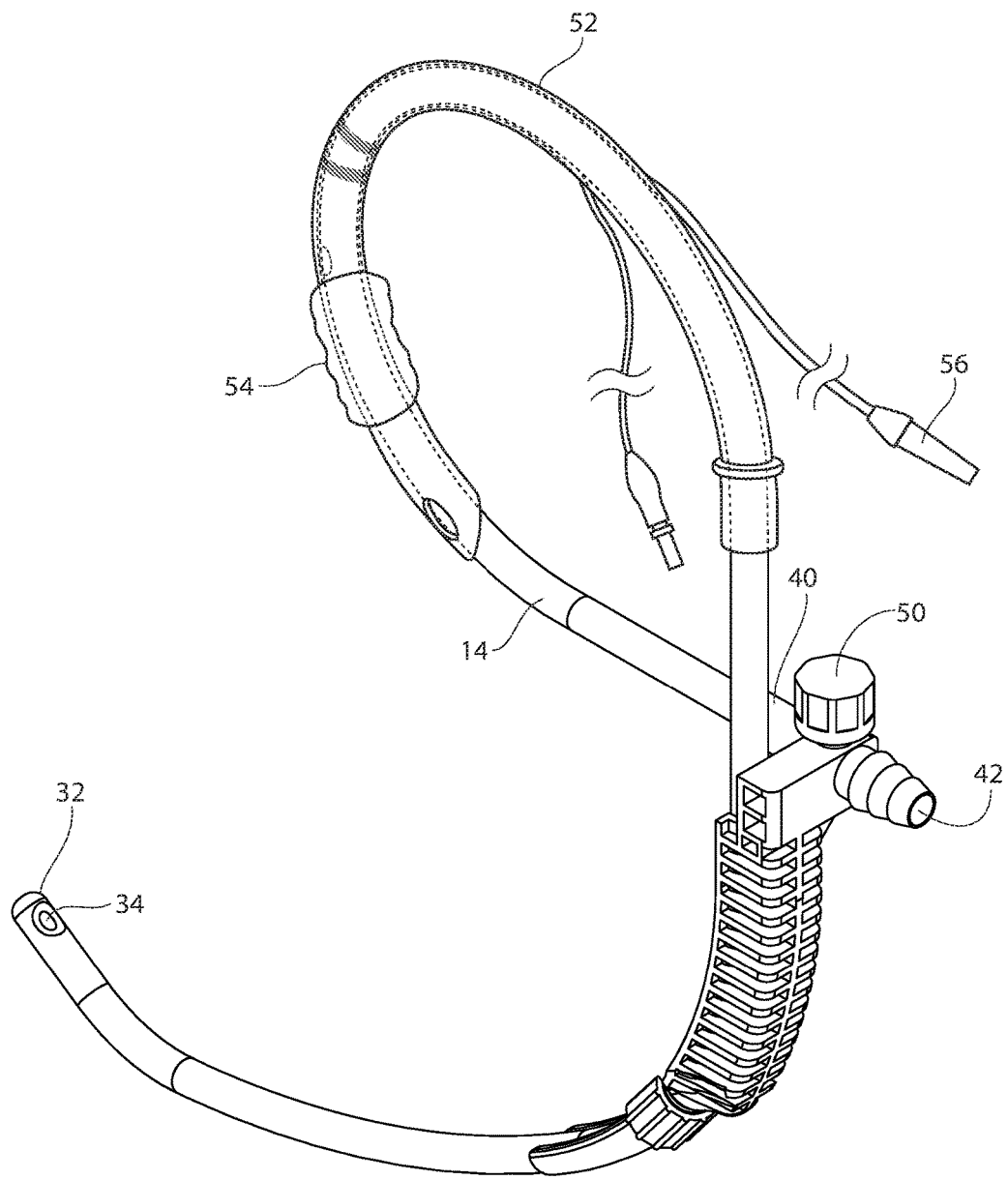
FIG. 12 is another perspective view of the device as shown in FIG. 10, with the device further supporting intubation tubing.

FIG. 12 further exemplifies the use of the gripping device 12 in connection with the intubation tubing 52. The intubation tubing 52 is shown supported by the bougie 14, with the gripping device 12 allowing the bougie in a coiled arrangement, as previously discussed. The arrangement also allows for the potential use of a balloon 54, which may inserted along with the tubing into the trachea for certain procedures, and inflated by way of vent 56, if necessary.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. A device for gripping a bougie, said bougie capable of forming a one-loop coil during an intubation process of a patient's airway, the device comprising:

a body having a top end and a bottom end, the body further having an inner surface forming a side opening and an exterior surface;

wherein the side opening of the inner surface comprises a longitudinally curved groove for receiving and retaining a bougie during the intubation process, a rotatable locking ring for securing said bougie within the groove during the intubation process;

wherein the bougie is maintained in a curved position inside said curved groove during said intubation process.

2. The device according to claim 1, wherein the exterior surface comprises a gripping area, said gripping surface being located on the opposite side of device as said side opening.

3. The device according to claim 2, wherein the gripping area comprises a plurality of ridges.

4. The device according to claim 1, wherein the groove has a semicircle shape, said semicircle shape extending to said bottom end of said body.

5. A method of intubation comprising the steps of:
providing a device according to claim 1;
squeezing a bougie into said curved groove, said squeezing carried out with gripping force of a users fingers;
gripping said device, thereby keeping said bougie in curved position within said curved group;
gripping said bougie and said gripping device as one unit during said intubation;
positioning the bougie during the intubation process within an airway.

6. The method of claim 5 wherein the device according to claim 1 further comprises:
a hollow connector, said connector having a first end for connecting to said bougie and a second end for connecting to an external delivery device, the method further comprising the steps of:
connecting said bougie to said first end;
connecting said second end to said external delivery device; and
providing suction through said bougie during said intubation method.

7. The method of claim 5, wherein the device according to claim 1 further comprises:
a hollow connector, said hollow connector having a first end for connecting to said bougie and a second end for connecting to an external device, the method further comprising the steps of:
connecting said bougie to said first end of said connector; and
connecting said second end of said connector to said external device.

8. The method according to claim 7, wherein said external device is an oxygen delivery device, the method further comprising the step of:
providing oxygen through said bougie during said intubation.

9. The method according to claim 7, where said external device is a suction device, the method further comprising the step of:
providing suction through said bougie during said intubation.

10. The method according to claim 9, wherein the connector allows for manual control of providing suction during said intubation.

11. The method of claim 5 further comprising the step of removing said device from said bougie while retaining said bougie in said airway.

12. A device for gripping a bougie, said bougie capable of forming a one-loop coil during an intubation process of a patient's airway, the device comprising:
a body having a top end and a bottom end, the body further having an inner surface forming a side opening and an exterior surface;
wherein the side opening of the inner surface comprises a longitudinally curved groove for receiving and retaining a bougie during the intubation process,
wherein the bougie is maintained in a curved position inside said curved groove during said intubation process; and
a hollow connector, said connector having a first end for connecting to said bougie and a second end for connecting to an external device.

13. The device according to claim 12 further comprising a suction control opening, said suction control opening intersecting said hollow connector, wherein said suction control opening provides for manual suction control during said intubation process.

14. The device according to claim 13, further comprising a removable cap located on said suction control opening.

15. The device according to claim 14, wherein said removable cap is securely attachable to said suction control opening, thereby allowing oxygen delivery through said bougie.

16. The device according to claim 12, wherein said connector is capable of receiving said bougie when said bougie forms said one-loop coil.

17. The device according to claim 16, wherein said one-loop coil capable of supporting an intubation tubing during said intubation process.

18. A device for gripping a bougie, said bougie capable of forming a one-loop coil during an intubation process of a patient's airway, the device comprising:
a body having a top end and a bottom end, the body further having an inner surface forming a side opening extending substantially from said top end to said bottom end of said body, and an exterior surface, said exterior surface comprises a gripping area, said gripping area being located on the opposite side of device as said side opening;
wherein the side opening of the inner surface comprises a longitudinally curved groove for receiving and retaining a bougie during the intubation process,
wherein the bougie is maintained in a curved position inside said curved groove during said intubation process.

19. The device according to claim 18, further comprising a rotatable locking ring for securing said bougie within the groove during the intubation process.

* * * * *